United States Patent [19]
Sherman et al.

[11] Patent Number: 5,624,441
[45] Date of Patent: *Apr. 29, 1997

[54] ATTACHMENT PLATE FOR TOP-TIGHTENING CLAMP ASSEMBLY IN A SPINAL FIXATION SYSTEM

[75] Inventors: Michael C. Sherman, Memphis; John A. Pafford, Bartlett, both of Tenn.; Richard B. Ashman, Dallas, Tex.

[73] Assignee: Danek Medical, Inc., Memphis, Tenn.

[*] Notice: The term of this patent shall not extend beyond the expiration date of Pat. No. 5,437,670.

[21] Appl. No.: 423,019

[22] Filed: Apr. 10, 1995

Related U.S. Application Data

[63] Continuation of Ser. No. 109,088, Aug. 19, 1993, Pat. No. 5,437,670.

[51] Int. Cl.$^6$ ............................................. A61B 17/70
[52] U.S. Cl. ............................................. 606/61; 606/60
[58] Field of Search ............................ 606/54, 59, 60, 606/61, 72

[56] References Cited

U.S. PATENT DOCUMENTS

| | | | |
|---|---|---|---|
| 4,653,481 | 3/1987 | Howland et al. | 606/61 |
| 4,655,199 | 4/1987 | Steffee | 606/61 |
| 5,246,442 | 9/1993 | Ashman et al. | 606/61 |
| 5,403,315 | 4/1995 | Ashman | 606/61 |
| 5,437,670 | 8/1995 | Sherman et al. | 606/61 |

*Primary Examiner*—Guy V. Tucker
*Attorney, Agent, or Firm*—Woodard, Emhardt, Naughton Moriarty & McNett

[57] ABSTRACT

An attachment plate for use with a spinal rod system converts a normally side-tightening eyebolt to a top-tightenable arrangement for engaging spinal fixation elements to the spinal rod. The plate is configured for use with spinal fixation elements having a posteriorly projecting central post, one lateral surface of the post contacting the spinal rod when the rod extends through an aperture of the eyebolt. The attachment plate is generally L-shaped with a slot in one portion for receiving the posteriorly projecting threaded post of the eyebolt. The plate includes a flange portion having a surface configured to engage the lateral surface of the fixation element post opposite the spinal rod. The attachment plate includes a camming segment to provide a clamping force component directed toward the flange portion of the plate to thereby tightly clamp the spinal rod to the fixation element post when a nut is threaded onto the eyebolt threaded post.

18 Claims, 2 Drawing Sheets

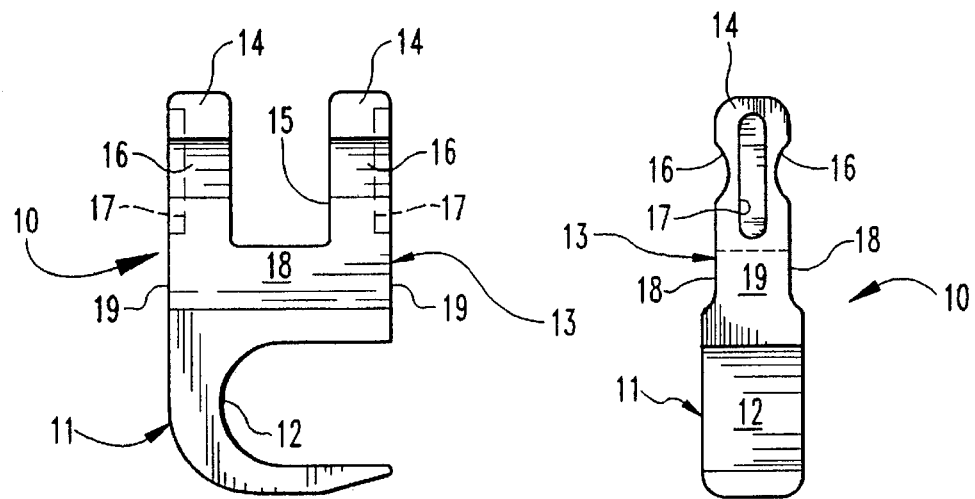
Fig. 3
Fig. 4
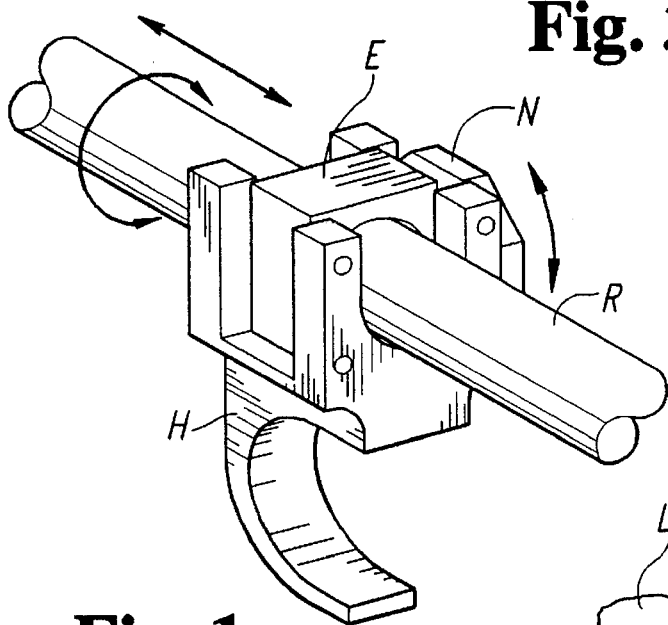
Fig. 1
*(Prior Art)*
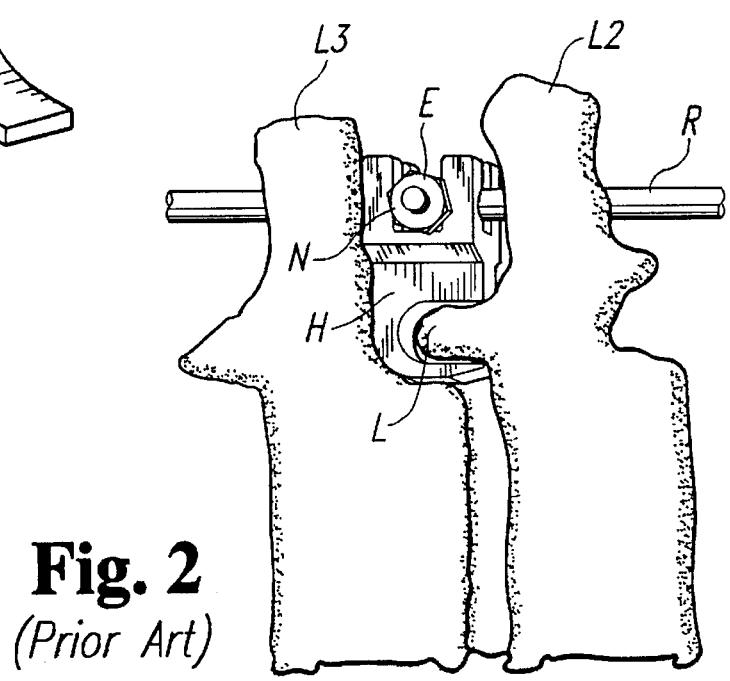
Fig. 2
*(Prior Art)*

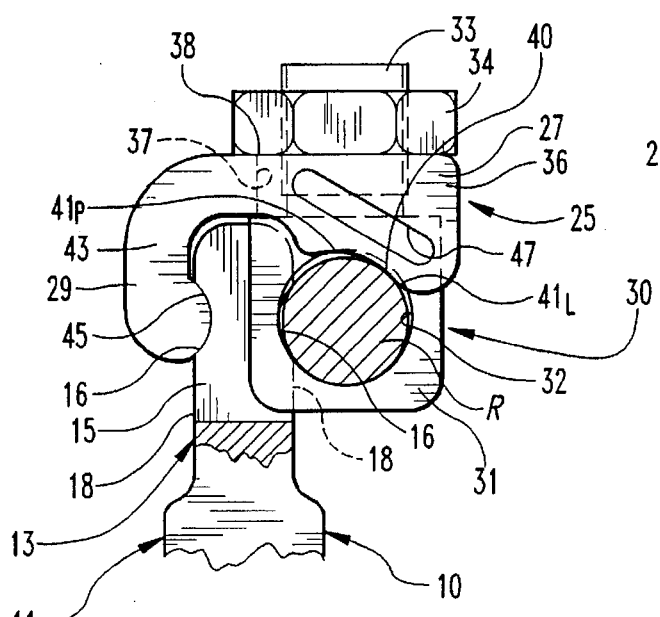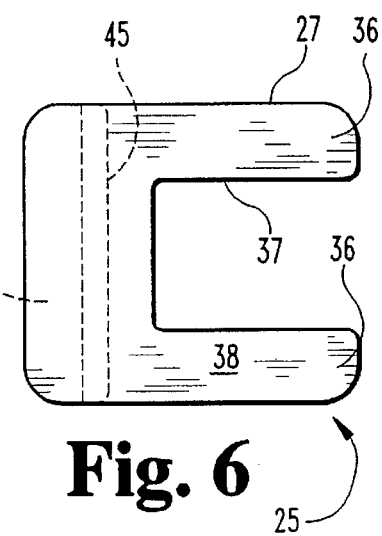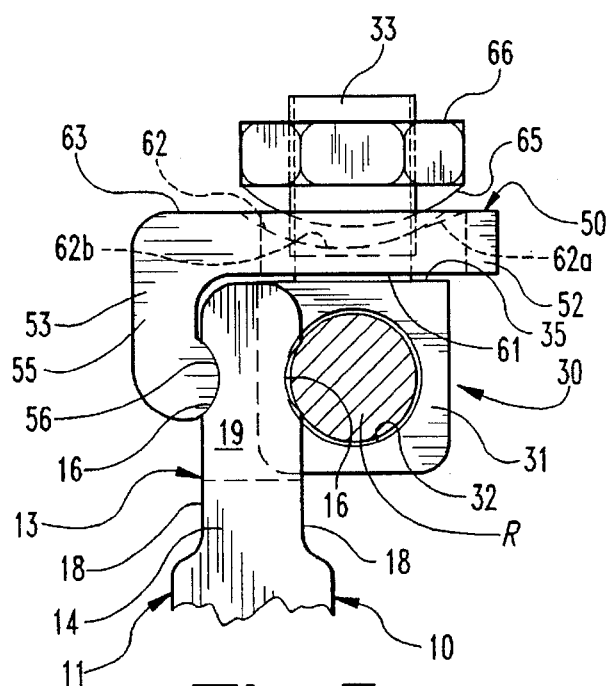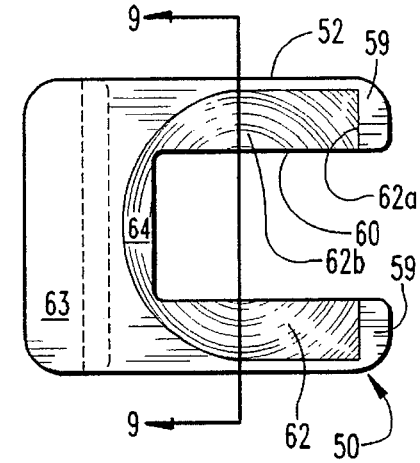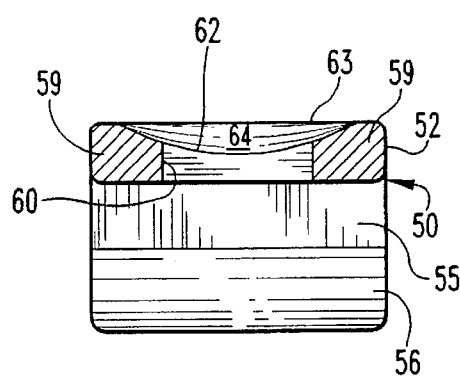

ATTACHMENT PLATE FOR TOP-TIGHTENING CLAMP ASSEMBLY IN A SPINAL FIXATION SYSTEM

This application is a continuation of application No. 08/109,088, filed Aug. 19, 1993 now Pat. No. 5,437,670.

BACKGROUND OF THE INVENTION

The present invention concerns spinal fixation systems, and particularly systems utilizing elongated rods adjacent the spinous process providing a base for connecting fixation elements to several vertebral levels. More specifically, the invention concerns improvements to the manner in which the vertebral fixation elements, such as spinal hooks and bone screws, are engaged to the elongated spinal rod.

Several techniques and systems have been developed for correcting and stabilizing spinal curves and facilitating spinal fusion. In one system, a bendable rod is longitudinally disposed adjacent the vertebral column, or spinous process, and is fixed to various vertebrae along the length of the column by way of a number or fixation elements. A variety of fixation elements can be provided which are configured to engage specific portions of the vertebra. For instance, one such fixation element is a spinal compression/distraction hook. This type of spinal hook is used to anchor the rod typically by engaging the laminae of the vertebra. Another fixation element is a spinal screw, which includes cancellous threads for engagement within the pedicle of a vertebra.

An example of a rod-type spinal fixation system under consideration with the present invention is the TSRH® spinal system sold by Danek Medical, Inc. In this system, a spinal hook, such as the hook H shown in FIG. 1 for example, is engaged to an elongated fixation rod R by way of an eyebolt assembly E. As is known in the art, the eyebolt E is mounted on the spinal rod and captured within yokes on the spinal hook. A nut N is then threaded onto a threaded post of the eyebolt to clamp the hook yoke between the nut and the fixation rod R. In this manner, the eyebolt E and the yokes of the hook H provide three degrees of fixation as represented by the arrows in FIG. 1. Details of the TSRH® spinal implant system are disclosed in the "TSRH® Surgical Technique Manual provided by Danek Medical, Inc., published in 1990, which disclosure is incorporated herein by reference.

It is the goal of the surgeon using spinal implant systems such as the Danek TSRH® system to apply vertebral fixation elements, such as a spinal hook or a bone screw, to the spine in appropriate anatomic positions, and then to engage each fixation element to the spinal rod. One problem with the spinal hooks H of the prior art, as represented in FIGS. 1 and 2, is that the hooks are rather bulky and wide since the fixation yokes of the hook are configured to surround the spinal rod R. Moreover it had been found that hooks of this type only allow the rod to be implanted in one position relative to the spinal column as dictated by the required position of the shoe of the hook against the vertebra.

In order to address that and other problems with the prior art systems shown in FIGS. 1 and 2, new spinal fixation elements have been developed which are the subject of pending applications assigned to the assignee of the present invention. One such fixation element, a spinal hook 10 shown in FIGS. 3 and 4, includes a shoe 11 having a bone engaging surface 12. The bone engaging surface 12 can be formed in any known shape to engage a laminae of a vertebra, for instance. Integral with the shoe 11 is a top portion 13 that forms a pair of posts 14 disposed apart from each other in the form of a U-shaped yoke to define a slot 15 therebetween. The slot 15 is wide enough to receive an eyebolt assembly therein, such as eyebolt assembly E shown in FIGS. 1 and 2. A pair of coaxial grooves 16 are formed in each lateral surface 18 of the hook 10 to receive a portion of a spinal rod, such as rod R shown in FIGS. 1 and 2. These rod grooves 16 are present on each opposite lateral surface 18 of the posts 14 so that the hook 10 can be oriented on either side of a spinal rod. Slots 17 are provided on each end face 19 for engagement by a hook-holding insertion instrument. The upper portion 13 and posts 14 can be referred to as a "central post" configuration of fixation element 10. A similar central post configuration can be utilized with fixation elements other than hooks, such as bone bolts or screws. Leaving the details of the newly developed central post vertebral fixation elements to its pending application, it can be appreciated that the central post hook 10, of FIGS. 3 and 4, has increased the versatility of rod-type spinal implant systems, such as the TSKH® system provided by Danek Medical. However, one feature consistent between this hook 10 and the prior art spinal hook H shown in FIG. 1, is that the eyebolt assembly E used to engage the fixation component to the spinal rod is "side-tightening". In other words, the threaded post of the eyebolt E and the nut N engaging the post both project laterally away from the spinal rod R when implanted in a patient, as specifically depicted in FIGS. 1 and 2. It has been found in practice that it is often cumbersome to engage the nut N with a wrench to tighten the nut onto the laterally projecting posts of the eyebolt assembly E. Moreover, space limitations at the implant site dictate that the wrench can only be moved through a partial turn before the handle of the wrench contacts the surrounding tissue. This necessitates taking the wrench off of the nut and re-engaging it for an additional partial rotation. Ratchet type wrench systems are typically not acceptable in procedures of this sort due to the risk of trauma to the surrounding tissue and the greater lateral clearance required to receive the ratchet mechanism at the surgical site.

In many procedures, it is desirable to utilize an eyebolt assembly, comprising the eyebolt E and nut N, for engaging the fixation elements to the spinal rod. These eyebolts are very convenient to the surgeon and are relatively easy and inexpensive to produce. One particular advantage of utilizing the eyebolt to engage the fixation element to the rod is the ability to provide a three-point clamp between the lop portion 13 of the fixation element 10 and the rod R. This three-point clamp restricts relative movement between these two components in all six degrees of freedom so that a rigid construct can be formed. While there are advantages to retaining the eyebolt assembly approach to connecting the fixation element to the rod, the prevailing disadvantage of the side-tightening aspect of this approach frequently makes use of an eyebolt assembly cumbersome.

Spinal and orthopaedic procedures are rapidly becoming prevalent surgeries, largely because of the high incidence of low back pain syndrome. In the past, surgical techniques for alleviating low back pain or for addressing spinal deformities or injuries has required fairly complicated and massive surgical techniques. The focus in recent times has been to greatly reduce the degree of invasion into the patient required for instrumenting a spine, as well as to reduce the amount of trauma to tissue surrounding the instrumentation, both during the procedure and after the spinal instrumentation has been implanted.

One cog in this worthwhile goal for minimally invasive spinal surgical techniques, is to provide an improved means for clamping the various vertebral fixation components to a spinal rod in a patient. Such a system should eliminate the side-tightening requirement of prior art systems to thereby minimize the intrusion into the patient. In addition, such a system should retain the versatility achieved by newly developed central post fixation elements. It is the goal of the present invention to address this and other concerns.

SUMMARY OF THE INVENTION

In accordance with the invention, an attachment plate is provided for use with a spinal rod system to convert a normally side-tightening eyebolt to a top-tightenable arrangement for engaging spinal fixation elements to the spinal rod. The plate is configured for use with spinal fixation elements having a posteriorly projecting o central post, one lateral surface of the post contacting the spinal rod when the rod extends through an aperture of the eyebolt. An eyebolt assembly is used to engage the fixation element to the spinal rod, which assembly includes an eyebolt body having an aperture for receiving the spinal rod and a threaded post projecting from the body to receive a nut threaded thereon.

In the preferred embodiments of the invention, the attachment plate is generally L-shaped with a slot in an eyebolt engaging portion for receiving the threaded post of the eyebolt. The plate further includes an anteriorly projecting clamping portion configured for engaging the fixation element post. The clamping portion includes a flange portion having a surface configured to engage the lateral surface of the fixation element post opposite the spinal rod.

The attachment plate includes a segment performing a camming function to provide a clamping force component directed toward the flange portion of the plate to thereby tightly clamp the spinal rod to the fixation element post when a nut is threaded onto the eyebolt threaded post. In one embodiment, the plate includes a lower surface with a cam portion oriented to contact the spinal rod with the attachment plate disposed between the rod and the eyebolt assembly nut. The cam portion is configured to urge the spinal rod toward the flange portion of the attachment plate as the eyebolt nut is tightened down on the eyebolt post against the upper surface of the attachment plate. In this manner, the eyebolt nut is top-tightenable, that is, accessible posteriorly when the system is implanted adjacent a patient's spine.

In another embodiment, the eyebolt engaging portion is generally a flat plate that includes a sloped recess in its upper surface adjacent the eyebolt nut. The recess is sloped toward the flange portion of the attachment plate. The eyebolt nut includes a spherical surface which is received within the recess in the attachment plate. As the nut is tightened down on the eyebolt post and against the attachment plate, the spherical nut surface advances down the sloped recess to its final seating position. Movement of the nut down the sloped recess forces the eyebolt closer to the fixation element post so that the spinal rod is clamped between the aperture of the eyebolt and the surface of the fixation element post.

The attachment plate provides means for converting an otherwise side-tightened eyebolt to a top-tightenable eyebolt, thereby greatly facilitating connection of spinal fixation elements to a spinal rod. In a typical fixation rod procedure, the spinal fixation element, such as a spinal hook, is engaged to a vertebra with its post projecting posteriorly. The spinal rod is disposed within the patient adjacent the post of the fixation element. An eyebolt is threaded onto the rod and is arranged on the rod adjacent the fixation element post with the eyebolt threaded post also projecting posteriorly. The attachment plate is then installed with the flange portion being first placed in contact with the post of the fixation element. The attachment plate is then pivoted anteriorly until the eyebolt engaging portion of the plate is aligned laterally across the spinal rod and eyebolt body with the eyebolt threaded post extending through the slot in the attachment plate. The eyebolt nut is then threaded onto the eyebolt threaded post until it contacts the attachment plate eyebolt engaging portion. The camming segments of the attachment plate urge the spinal rod into firm contact with the fixation element post as the nut is tightened further down against the attachment plate.

The attachment plate of the present invention provides a significant benefit in that it permits the use of eyebolts to engage fixation elements to a spinal rod, while providing means to allow top-tightening or the eyebolt nuts. Prior systems rely upon access to the nuts lateral to the components, or side-tightening. The present attachment plate allows the eyebolt to be rotated on the spinal rod so that the threaded eyebolt post is projecting posteriorly to a more readily accessible position for the surgeon. Further, tightening the eyebolt nut against the attachment plate increases the clamping force of the rod to the fixation element to produce a rigid construct.

It is then one object of the present invention to provide a system that can be used with existing spinal rod and eyebolt attachment systems to convert the eyebolts from a side-tightening to a top-tightening configuration. Another object is to provide an easily implanted and manipulated component at the surgical site that will streamline the implant procedure and reduce the amount of trauma suffered by the surrounding tissue over prior systems.

A further object of the present invention is to provide a component that enhances the clamping force between the spinal rod and the fixation element to form a rigid construct. Other objects and certain benefits of the present invention will become apparent from the following written description read in combination with the accompanying figures.

DESCRIPTION OF THE FIGURES

FIG. 1 shows a spinal hook of known design engaged to a fixation rod by way of an eyebolt assembly, as configured in accordance with one prior art system, the TSRH® spinal system.

FIG. 2 is a side view showing the prior art system depicted in FIG. 1 in which a standard fixation hook is engaged about the laminae of a lumbar vertebra.

FIG. 3 is a side elevational view of the spinal hook of recent design for which the top-tightening clamp assembly of the present invention is configured to engage.

FIG. 4 is an end elevational view of the spinal hook shown in FIG. 3.

FIG. 5 is a side elevational view of the attachment plate assembly in accordance with one embodiment of the present invention, shown clamping a spinal hook of the type shown in FIG. 4 to a spinal rod.

FIG. 6 is a top elevational view of the attachment plate shown in FIG. 5.

FIG. 7 is a side elevational view of an alternative embodiment of the attachment plate in accordance with the present invention.

FIG. 8 is a top elevational view of the attachment plate shown in FIG. 7.

FIG. 9 is an end cross-sectional view of the attachment plate shown in FIG. 8 taken along line 9—9 as viewed in the direction or the arrows.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

As discussed in the background of the invention, the present invention contemplates a system for engaging a vertebral fixation element to a spinal rod. More particularly, the fixation element is configured as shown in FIGS. 3 and 4 having a top portion 13 that forms a pair of posts 14 defining a slot 15 therebetween in a "central post" configuration. It is understood that although in the specific embodiments disclosed herein the fixation element is a spinal hook, the same "central post" approach can be applied to other types of vertebral fixation components, such as a bone screw. Whether the fixation element is a hook or a screw, it is engaged with the vertebra first and then clamped to the spinal rod using an eyebolt assembly.

In accordance with the present invention, an attachment plate 25 is provided which includes an eyebolt engaging portion 27 and a fixation element clamping portion 29. An eyebolt assembly 30 is provided which is modified somewhat from the eyebolt E shown in FIG. 1. In particular, the eyebolt assembly 30 includes an eyebolt body 31 having a central aperture 32 therethrough for receiving a spinal rod R therethrough. A threaded post 33 projects from a surface of the eyebolt body 31. The post 33 is adapted to engage a machine threaded nut 34 in a known manner. A central difference between this eyebolt assembly 30 and other more conventional eyebolts is that the threaded post 33 is longer so that it can receive the attachment plate 25 thereon.

In one preferred embodiment, the attachment plate 25, and particularly the eyebolt engaging portion 27 is forked, as shown in FIG. 6. Specifically, the eyebolt engaging portion includes a pair of arms 36 which define a slot 37 therebetween. The slot 37 is wide enough to receive at least the threaded post 33 of the eyebolt assembly 30 therethrough. The eyebolt engaging portion 27 also includes an upper surface 38 against which the eyebolt nut 34 is threaded. The width of slot 37 cannot exceed the flat width of the nut 34 and is preferably sufficiently narrower than the nut to provide solid purchase against the upper surface 38 when the nut is tightened thereon.

In the specific embodiment shown in FIG. 5, the eyebolt engaging portion 27 further includes a lower rod engaging surface 40. This rod engaging surface is formed on each of the arms 36 and is preferably curved to accommodate the spinal rod R, and to operate as a cam surface as described herein. In one specific embodiment, the lower rod engaging surface 40 spans about one-fifth of the circumference of the spinal rod. Most of the rod engaging surface 40 contacts the spinal rod K at a posterior surface $41_p$ (as viewed when engaged within the patient), and further includes a segment lateral to the spinal rod, which segment is designated $41_L$ in FIG. 5. As will be explained more fully herein, the rod engaging surface, and particularly the lateral segment $41_L$, acts as a camming surface to provides a firm clamping force against the spinal rod R.

The attachment plate 25 further includes a fixation element clamping portion 29 which is more particularly defined by an anterior projecting flange 43. The end of the flange 43 is formed into a projection 45 which is configured to engage the coaxial grooves 16 in one lateral surface 18 of the fixation element 10. In the specific embodiment of FIG. 5, this projection 45 has a curvature substantially identical to the curvature of the coaxial grooves 16 so that the projection will fit snuggly within the grooves when the assembly is completed. The attachment plate 25 includes insertion instrument slots 47 in the eyebolt engaging portion, and particularly in opposite faces of the arms 36. As with the fixation element, the instrument holding slots 47 provide a means for the plate to be held by an insertion instrument during the instrumentation procedure.

From the foregoing description of the attachment plate 25 and its relation to the fixation element and rod, the manner of use of the plate should be readily apparent. It is contemplated with use of the present invention that the surgeon would have already positioned various fixation elements, such as hook 10, at appropriate vertebral levels. A properly positioned fixation element will have its top portion 13, and particularly the central posts 14, projecting posteriorly. Several eyebolt bodies 31 can be pre-threaded onto the spinal rod prior to its location adjacent the spine. As the spinal rod or the vertebral column is manipulated to position the fixation elements in contact with the spinal rod R, each eyebolt body 31 is positioned between the posts 14 of a corresponding fixation element 10 so that the rod R, extending through the eyebolt aperture 32 contacts the coaxial grooves 16 on one side of the hook central posts 14. Further, the eyebolt body is situated so that its threaded post 33 also projects posteriorly for easy access by the surgeon.

With the threaded post 33 projecting posteriorly, the attachment plate 25 is top-loaded over the eyebolt assembly 30 and in contact with the fixation element 10. More particularly, the attachment plate 25 is loaded so that the projection 45 first engages the coaxial groove 16 on the side of the central posts 14 opposite the rod R engagement. The attachment plate is then pivoted anteriorly so that the lower rod engaging surface 40 contacts the spinal rod K as it is situated directly adjacent the fixation element 10. Some manipulation may be required to bring the rod R into contact with the fixation element 10, while simultaneously contacting the lower rod engaging surface 40 of the attachment plate 25. Preferably, the slot 37 defined between the arms 36 is open at its end (as depicted in FIG. 6) to readily receive the eyebolt threaded post therein as the plate is pivoted anteriorly. Alternatively, the slot 37 can be closed at both ends. A closed slot 37 increases the complexity of the installation of the plate by requiring that the eyebolt assembly 30 be rotated about the rod R somewhat so the post 33 is oriented at an angle. With the post 33 so oriented, the slot 37 will slide over the post 33 when the plate is rotated. As the plate 25 is rotated closer to the rod, the post 33 will also naturally rotate to its normal installed posterior facing position.

With the three components (fixation element 10, spinal rod K and attachment plate 25) in intimate contact, the nut 34 is threaded onto the post 33 until it engages the posteriorly facing upper surface 38 of the attachment plate 25. As the nut 34 is threaded further and more tightly onto the eyebolt post 33, the fixation element top portion 13 and spinal rod R are clamped between the projection 45 and the lower rod engaging surface 40 of the attachment plate 25.

It can thus be seen that the attachment plate 25 provides a ready means for converting an otherwise side loading eyebolt assembly into a top-loading eyebolt assembly for engaging a fixation element. The slot 37 in the attachment plate 25 allows for easy manipulation of the eyebolt and spinal rod relative to the fixation element until final clamping is desired. As the nut 34 is threaded onto the post 33 of the eyebolt assembly 30, the lower rod engaging surface 40, and particularly the lateral segment $41_L$, acts as a camming surface to gradually urge the spinal rod R into a firmer engagement with the coaxial groove 16 on one lateral surface 18 of the fixation element 10. The lateral segment $41_L$ provides a clamping force component directed toward the clamping portion flange 43 and particularly toward the projection 45. Simultaneously, the clamp engagement between the projection 45 and coaxial groove 16 on the other side of the fixation element is also increased.

As indicated, in the preferred embodiment the rod engaging surface 40, including the lateral segment $41_L$, is curved, preferably at approximately the same radius as the spinal rod. Alternatively, the lateral segment $41_L$ can assume other configurations, provided that a lateral clamping force component is exerted by the rod engaging surface 40 against the spinal rod R. For example, a lateral segment $41_L$ that is oriented at an angle relative to both the posterior and lateral directions will provide such a clamping force component as the rod r( slides against the angled segment.

An alternative embodiment of the present invention is shown in FIGS. 7 through 9. Specifically, an attachment plate 50 is shown which does not include the same lower rod engaging surface 40 as the attachment plate 25 of FIG. 5. The attachment plate 50 does include an eyebolt engaging portion 52 and a fixation element clamping portion 53. The fixation element clamping portion 53 also includes an anterior protecting flange 55 terminating in a projection 56 which is configured to engage the coaxial groove 16 in one lateral surface 18 of the fixation element 10.

As with the attachment plate 25, the plate 50 includes a pair of arms 59 which define a slot 60 therebetween configured to receive the threaded post 33 of the eyebolt assembly 30 therethrough. In this embodiment, the slot 60 is narrower than the eyebolt body 31 so the lower surface 61 of the plate 50 can contact the upper surface 35 of the eyebolt body. Further, instead of the camming action provided by the lower rod engaging surface 40 of the plate 25, the attachment plate 50 includes a sloped recess 62 defined in the upper surface 63 of the eyebolt engaging portion 52. This sloped recess 62, or camming surface, is configured to engage a lower spherical surface 65 of a specially configured nut 66.

As can be seen more clearly in FIG. 7, the recess 62 slopes from end 62a at the open end of the arms 59 toward the portion 62b adjacent the inner end of the slot 60. In other words, the recess 62 slopes toward the anteriorly projecting flange 55 so that the eyebolt nut 66 is drawn in that direction as it is tightened onto the threaded post. This sloped recess 62 serves the same camming function as the lower rod engaging surface 40 of the previous embodiment. More particularly, as the nut 66 is threaded onto the post 33, the lower spherical surface 65 contacts the sloped recess 62. As it is threaded further onto the threaded post 33, the spherical surface 65 gradually slides down the sloped recess 62 until it seats at the end portion 64 of recess 62 the attachment plate 50. In effect, then the interaction between the lower spherical surface 65 of the nut 66 and the sloped recess 62 of the attachment plate 50 draws the threaded post 33 closer to the fixation element 10. The eyebolt body 31 naturally follows with the threaded post 33 so that the body too is forced closer to the fixation element central post 15. In this manner the spinal rod R is forced to contact the walls of the aperture 32 of the eyebolt body 31 generally lateral to the fixation element 10 at the same time that the rod R contacts the groove 16 in the one surface of the fixation element post 15. The rod R is then clamped between the eyebolt and the fixation element 10, while the fixation element 10, and more particularly the central post 14, is clamped between the projection 56 of the attachment plate and the spinal rod R The plate itself is clamped between the upper surface 35 of the eyebolt body and the nut 66. The attachment plate 50 is loaded and engaged to the fixation components in a manner similar to that described in connection with attachment plate 25 of the previous embodiment.

The attachment plates 25 and 50 are preferably formed of 316L stainless steel having a tensile strength of about 125 ksi. However, other biocompatible materials may be suitable for forming the attachment plate. While the generally L-shaped configuration of the plates 25 and 50 facilitate installation of the plates, this same shape can lead to stress concentrations at the intersection between the eyebolt engaging portion and the anterior projecting flange. The plates must be strong enough to withstand bending, particularly at the joint between the flange 43 and the eyebolt engaging portion, such as portion 27 of the plate 25. The internal and external corners at this joint between the two portions are preferably rounded, as shown in FIGS. 5 and 7, to reduce the likelihood of stress concentrations forming at that intersection. It is understood that this portion of the attachment plate 25 will endure a significant amount of load as the entire assembly is tightened to rigidly clamp the fixation element 10 to the spinal rod R.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A top-loaded attachment plate for use with a spinal fixation system that includes an eyebolt with an aperture and a threaded post, a spinal rod extending through the aperture, a nut engaging the post, and a vertebra fixation element having a vertebra engaging portion and a rod engaging portion with opposite surfaces, one of the opposite surfaces contacting the spinal rod, said attachment plate comprising:

a plate body having an upper surface and an opposite lower surface and defining an elongated slot through said upper and lower surfaces, said elongated slot having a closed end and an open end opposite said closed end, said open end being configured to slidingly receive the eyebolt threaded post therein;

a flange projecting from said lower surface of said body, said flange being generally perpendicular to at least a portion of said lower surface, said flange having end positioned anterior to said slot, said end having a curved end surface being configured for contacting the rod engaging portion of the vertebra fixation element at the other of the opposite surfaces: and wherein at least one of said upper and lower surfaces defines a cam segment to promote clamping of the vertebra fixation element between the rod and said flange when the nut is threaded on the post of the eyebolt.

2. The top-loaded attachment plate of claim 1, wherein said flange is adjacent said closed end of said slot.

3. The top-loaded attachment plate of claim 1, wherein said body includes a pair of arms which define said slot therebetween.

4. The top-loaded attachment plate of claim 3, wherein each of said pair of arms has a face defining an instrument holding slot.

5. The top-loaded attachment plate of claim 1, wherein said cam segment is defined by a portion of said lower surface curved to correspond to the curvature of the spinal rod for engagement therewith.

6. The top-loaded attachment plate of claim 1, wherein said cam segment includes a sloped recess defined by a portion of said upper surface, said sloped recess being configured for engagement by a lower spherical surface of the nut.

7. A top-loaded attachment plate for use with a spinal fixation system that includes an eyebolt with an aperture and a threaded post, a spinal rod extending through the aperture, a nut engaging the post, and a vertebra fixation element having a vertebra engaging portion and a rod engaging portion with opposite surfaces, one of the opposite surfaces contacting the spinal rod, said attachment plate comprising:

a plate body having an upper surface and an opposite lower surface and defining an elongated slot between said upper and lower surfaces;

a flange projecting generally perpendicularly from said lower surface of said body, said flange having a curved end surface anterior to said slot, said curved end surface being configured for contacting the rod engaging portion of the vertebra fixation element at the other of the opposite surfaces; and a cam segment defined by a portion of said lower surface curved to correspond to the curvature of the spinal rod for engagement therewith.

8. The top-loaded attachment plate of claim 7, wherein said cam segment is configured to span about one fifth the circumference of a cylindrically shaped spinal rod.

9. The top-loaded attachment plate of claim 7, wherein said elongated slot has a closed end and an open end opposite said closed end, said open end being configured to slidingly receive the eyebolt threaded post therein.

10. The top-loaded attachment plate of claim 9, wherein said flange is adjacent said closed end of said slot.

11. The top-loaded attachment plate of claim 7, wherein said body includes a pair of arms which define said slot therebetween.

12. The top-loaded attachment plate of claim 11, wherein each of said pair of arms has a face defining an instrument holding slot.

13. A top-loaded attachment plate for use with a spinal fixation system that includes an eyebolt with an aperture and a threaded post, a spinal rod extending through the aperture, a nut with a lower spherical surface engaging the post, and a vertebra fixation element having a vertebra engaging portion and a rod engaging portion with opposite surfaces, one of the opposite surfaces contacting the spinal rod, said attachment plate comprising:

a plate body having an upper surface and an opposite lower surface and defining an elongated slot between said upper and lower surfaces;

a flange projecting generally perpendicularly from said lower surface of said body, said flange having a curved end surface anterior to said slot, said curved end surface being configured for contacting the rod engaging portion of the vertebra fixation element at the other of the opposite surfaces; and a cam segment including a sloped recess defined by an eyebolt engaging portion of said upper surface, said sloped recess being configured for engagement by the lower spherical surface of the nut.

14. The top-loaded attachment plate of claim 13, wherein said elongated slot has a closed end and an open end opposite said closed end, said open end being configured to slidingly receive the eyebolt threaded post therein.

15. The top-loaded attachment plate of claim 14, wherein said flange is adjacent said closed end of said slot.

16. The top-loaded attachment plate of claim 13, wherein said sloped recess includes a downward slope from said open end toward closed end.

17. The top-loaded attachment plate of claim 13, wherein said body includes a pair of arms which define said slot therebetween.

18. The top-loaded attachment plate of claim 17, wherein each of said pair of arms has a face defining an instrument holding slot.

\* \* \* \* \*